United States Patent
Dunn et al.

(10) Patent No.: US 10,811,137 B2
(45) Date of Patent: Oct. 20, 2020

(54) COMPREHENSIVE DIAGNOSIS AND CARE SYSTEM

(71) Applicant: Redivus Health LLC, Olathe, KS (US)

(72) Inventors: Jeff Dunn, Overland Park, KS (US); Heath Latham, Overland Park, KS (US); Achal Desai, Overland Park, KS (US); Anthony Fangman, Overland Park, KS (US); David Elliott, Gardner, KS (US)

(73) Assignee: Redivus Health LLC, Olathe, KS (US)

( * ) Notice: Subject to any disclaimer, the term of this patent is extended or adjusted under 35 U.S.C. 154(b) by 835 days.

(21) Appl. No.: 15/017,072

(22) Filed: Feb. 5, 2016

(65) Prior Publication Data
US 2016/0232310 A1    Aug. 11, 2016

Related U.S. Application Data

(60) Provisional application No. 62/113,473, filed on Feb. 8, 2015.

(51) Int. Cl.
*G06Q 30/04*    (2012.01)
*G16H 50/20*    (2018.01)
(Continued)

(52) U.S. Cl.
CPC ............. *G16H 50/20* (2018.01); *G06F 19/00* (2013.01); *G06Q 30/04* (2013.01); *G16H 50/30* (2018.01)

(58) Field of Classification Search
CPC .... G06F 19/00; G06F 19/325; G06F 19/3418; G06F 19/30; G06F 17/2785;
(Continued)

(56) References Cited

U.S. PATENT DOCUMENTS

| | | | |
|---|---|---|---|
| 2006/0173663 A1* | 8/2006 | Langheier | G16H 50/20 703/11 |
| 2007/0033073 A1* | 2/2007 | Tajaliawal | G06Q 50/22 705/3 |

(Continued)

FOREIGN PATENT DOCUMENTS

WO    2012-122196 A2    9/2012

OTHER PUBLICATIONS

PCT Patent Application PCT/US2016/0168341 International Search Report and Written Opinion dated Jun. 2, 2016, 7 pages.

*Primary Examiner* — Maroun P Kanaan
(74) *Attorney, Agent, or Firm* — Erise IP, P.A.

(57) ABSTRACT

A diagnostic care coordination system assists a caregiver with treating a patient. The system comprises a diagnostic engine and a care engine. The diagnostic engine is configured to generate a working diagnosis of the patient. The diagnostic engine includes a static diagnosing web containing a plurality of information nodes and a dynamic diagnosing analyzer for presenting to a user a plurality of information requests. The dynamic diagnosing analyzer navigates a user through the plurality of information nodes of the static diagnosing web based upon received responses to said plurality of information requests. Based upon a route through the static diagnosing web as taken by the dynamic diagnosing analyzer, the diagnostic engine generates the working diagnosis. The care engine determines a treatment plan based upon said working diagnosis.

20 Claims, 9 Drawing Sheets

(51) Int. Cl.
*G16H 50/30* (2018.01)
*G06F 19/00* (2018.01)

(58) Field of Classification Search
CPC ............ G06F 16/3329; G06F 16/3344; G06F 16/24578; G06F 17/277; G16H 50/20; G16H 50/50; G16H 40/20; G16H 10/60; G16H 50/70; G16H 10/20; G16H 50/30; G06N 20/00; G06Q 50/24; A61B 5/14532; A61B 5/7275; A61B 2505/03; A61B 5/0205; A61B 5/024
See application file for complete search history.

(56) References Cited

U.S. PATENT DOCUMENTS

| | | | |
|---|---|---|---|
| 2008/0177578 A1 | 7/2008 | Zakim | |
| 2014/0249850 A1* | 9/2014 | Woodson | G06F 19/3481 705/3 |
| 2014/0365232 A1* | 12/2014 | Sadeghi | G16H 50/20 705/2 |
| 2015/0238692 A1* | 8/2015 | Peterson | A61N 1/046 604/503 |

* cited by examiner

Hyponatremia Dx

Serum Osmo
- <280
- 280-300
- >300

Volume Status
- Euvolemia ∧

Urine NA > 20
- Yes
- No
- Unsure

Uosm < 100
- Yes
- No
- Unsure

Calculator | Feedback

FIG. 4D

Hypervolemia — edema in extremities, ascites, pulmonary vascular congestion, +JVD

Euvolemia — normal body fluid volume

Hypovolemia — orthostatic, increased BUN/Cr ratio >20, tachycardia, decreased urine output

Unsure

[Screen 1 — FIG. 4E]

●●●●○ Verizon 📶  11:53 AM  ✴ 🔋

< Back    Hyponatremia Tx    ☆

1) Is the patient hypervolemic with hyponatremia (CHF, Liver Failure, ESRD)?

Vasopressin antagonists can be used in hypervolemic/euvolemic hyponatremia associated with chf, siadh with Na<125, sx hyponatremia, or resistant cases. Contraindicated in hypovolemic hyponatremia

| No | Yes |

| Calculator |

If patient has: chronic hyponatremia, Sodium<105, Hypokalemia, Alcoholism, Malnutrition, Liver Disease then HIGH RISK of Osmotic Demyelination Syndrome

| Calculator | Feedback |

FIG. 4E

[Screen 2 — FIG. 4F]

●●●●○ Verizon 📶  11:54 AM  ✴ 🔋

< Back    Hyponatremia Tx    ☆

| No | Yes |

Treat the hypervolemia consider diuresis and possibly Vasopressin antangonists if indicated.

2) Is the patient hyponatremic with water intoxication or has Beer Drinkers Potomania?

| No | Yes |

3) Is the patient symptomatic with sodium less than 120?

| Mild-Moderate ▲ |

Treatment rate 8-10MEQ/24 hrs, check sodium every 2-4 hours

4) Is this acute (occurred in <48 hours) or chronic >48 hours?

| Calculator | Feedback |

Hyponatremia Tx

- 24 hour correction (Meq in): 6Meq | 10Meq | 12Meq
- Initial Rate of Correction (Meq/liter/hour): 0.25 | 0.4 | 1.0
- Age/Gender Factor: Elderly Woman (0.45)
- Initial Hours to Correct: 2 | 4 | 6
- Weight (kg): 100
- Initial Rate of Correction (Meq/...)
- Calculator | Feedback

FIG. 4G

Hyponatremia Tx — Home

Classic | Adrogue

- Sodium (Meq/Liter):
- 24 hour correction (Meq in): 6Meq | 10Meq | 12Meq
- Initial Rate of Correction (Meq/liter/hour): 0.25 | 0.4 | 1.0
- Age/Gender Factor: Elderly Woman (0.45)
- Initial Hours to Correct: 2 | 4 | 6
- Calculator | Feedback

| ●●●●○ Verizon 📶 11:56 AM 🔋 |
|---|
| < Back   Hyponatremia Tx   Home |

Results

Change in Sodium    | 1 Meq/Liter |
in first 4 hrs

Change in Sodium    | 9 Meq/Liter |
in last 20 hrs

Goal Sodium         | 22 Meq/Liter |
in 24 hrs

Initial rate of Infusion   | 73.1 ml/hr |
in first 4 hrs

Estimated Secondary Rate of Infusion   | 131.5 |
in last 20 hrs
(adjust based on every 2-4 hr sodium level)
Check Serum Sodium Every 2 hours for Severe Hyponatremia
Check Serum Sodium Every 4 hours for all others

| Calculator | Feedback |

FIG. 4I

COMPREHENSIVE DIAGNOSIS AND CARE SYSTEM

RELATED APPLICATIONS

This non-provisional patent application claims priority benefit, with regard to all common subject matter, of earlier-filed U.S. Provisional Patent Application No. 62/113,473, filed on Feb. 8, 2015, and entitled "METHOD OF TREATING A PATIENT." The identified earlier-filed provisional patent application is hereby incorporated by reference in its entirety into the present application.

BACKGROUND

1. Field

Embodiments of the invention are broadly directed to determining a diagnosis, an etiology, and a treatment plan for a patient. More specifically, embodiments of the invention are directed to a diagnostic care coordination system for assisting a caregiver.

2. Related Art

The diagnosis and care of patients is a vastly complex and ever-changing field. The number and types of diagnoses and treatment plans are beyond the scope of any doctor or other care provider to know and instantly access. Further, there are numerous specialties and disciplines that are not immediately available to the care provider. This can lead to errors and delays in treatment.

Medical malpractice is a growing problem for a few reasons. First, it is difficult to track and document the procedures, decisions, and diagnoses. Systems of the prior art are all retrospective (i.e., looking back to record something that previously happened). This is prone to error and easily questioned by patients. Second, the scope of medical knowledge combined with the speed and accuracy that is necessary to save a life is dauntingly complex. Minor mistakes and delays can cause severe injury and death. Systems of the prior art rely on the doctor or other care provider to keep all of this vast knowledge within their mind to be brought forth instantly and correctly every time. Unfortunately, this is an unrealistic expectation. Further, the precise calculation of the appropriate dosing levels and frequency is a complex analysis beyond human computation. As such, care providers often either follow generic guidelines or use a trial-and-error customization for the patient. The former can be ineffective (as level and frequency can vary by patient type and other conditions), and the latter can be dangerous.

What is lacking in the prior art is a tool to assist a doctor or other care provider with efficiently diagnosing and precisely treating a medical patient, while also recording how, why, and when the diagnosis and treatment were selected.

SUMMARY

Embodiments of the invention solve the above-mentioned problems by providing a diagnostic care coordination system for assisting a caregiver with diagnosing and caring for a patient. The diagnostic care coordination system is quick, easy to use, repeatable, educational, and simplistic for the user. The diagnostic care coordination system reduces medical malpractice, duplicative tests and procedures, record ambiguities, and medical delays so as to improve patient and user experience. For example, embodiments of the invention may be provided on a smart phone, tablet, or smart watch so as to actively assist the caregiver while the caregiver is diagnosing and caring for the patient.

Embodiments of the invention are directed to a diagnostic care coordination system for assisting with treating a patient, the system comprising a diagnostic engine and a care engine. The diagnostic engine is configured to generate a working diagnosis of the patient. The diagnostic engine includes a static diagnosing web containing a plurality of information nodes and a dynamic diagnosing analyzer for presenting to a user a plurality of information requests. The dynamic diagnosing analyzer navigates a user through the plurality of information nodes of the static diagnosing web based upon received responses to said plurality of information requests. Based upon a route through the static diagnosing web as taken by the dynamic diagnosing analyzer, the diagnostic engine generates the working diagnosis. The care engine determines a treatment plan based upon said working diagnosis. The treatment plan includes a set of care steps. The care engine oversees administration of the set of care steps to determine whether a patient response to the treatment plan is consistent with the working diagnosis.

Embodiments of the invention are directed to a diagnostic engine for assisting with treating a patient, the diagnostic engine comprising a static diagnosing web and a dynamic diagnosing analyzer. The static diagnosing web contains a plurality of information nodes. The dynamic diagnosing analyzer presents to a user a plurality of information requests based upon the information nodes. The dynamic diagnosing analyzer navigates a user through the information nodes of the static diagnosing web based upon received responses from said plurality of information requests. Based upon a route through the static diagnosing web as taken by the dynamic diagnosing analyzer, the diagnostic engine generates a working diagnosis, which includes a working etiology indicative of a cause or source of the working diagnosis.

Embodiments of the invention are also directed to a non-transitory computer readable medium having a computer program stored thereon for assisting in treating a patient as a care engine, wherein the computer program instructs at least one processing element to perform the following steps: acquiring a working diagnosis for the patient; determining a treatment plan, wherein the treatment plan includes a set of care steps; assigning a timestamp to each care step performed, wherein the care engine oversees administration of the set of care steps to determine whether a patient response to the treatment plan is consistent with the working diagnosis; and sending, based upon a finding that the patient response is inconsistent with the working diagnosis, information indicative of patient response to a diagnosing engine.

Other embodiments may be directed to a computerized method of performing the discussed steps (such as diagnosing a patient, treating a patient, caring for a patient, etc.), a dedicated device (such as a tablet computer, mobile phone or a smart watch) acting as the diagnostic care coordination system, etc.

This summary is provided to introduce a selection of concepts in a simplified form that are further described below in the detailed description. This summary is not intended to identify key features or essential features of the claimed subject matter, nor is it intended to be used to limit the scope of the claimed subject matter. Other aspects and advantages of the invention will be apparent from the following detailed description of the embodiments and the accompanying drawing figures.

BRIEF DESCRIPTION OF THE DRAWING FIGURES

Embodiments of the invention are described in detail below with reference to the attached drawing figures, wherein:

FIG. 4A-4I are screen captures illustrating an exemplary function of the dynamic diagnosing analyzer, specifically illustrating a diagnosis and treatment plan for hyponatremia.

Figure 1:
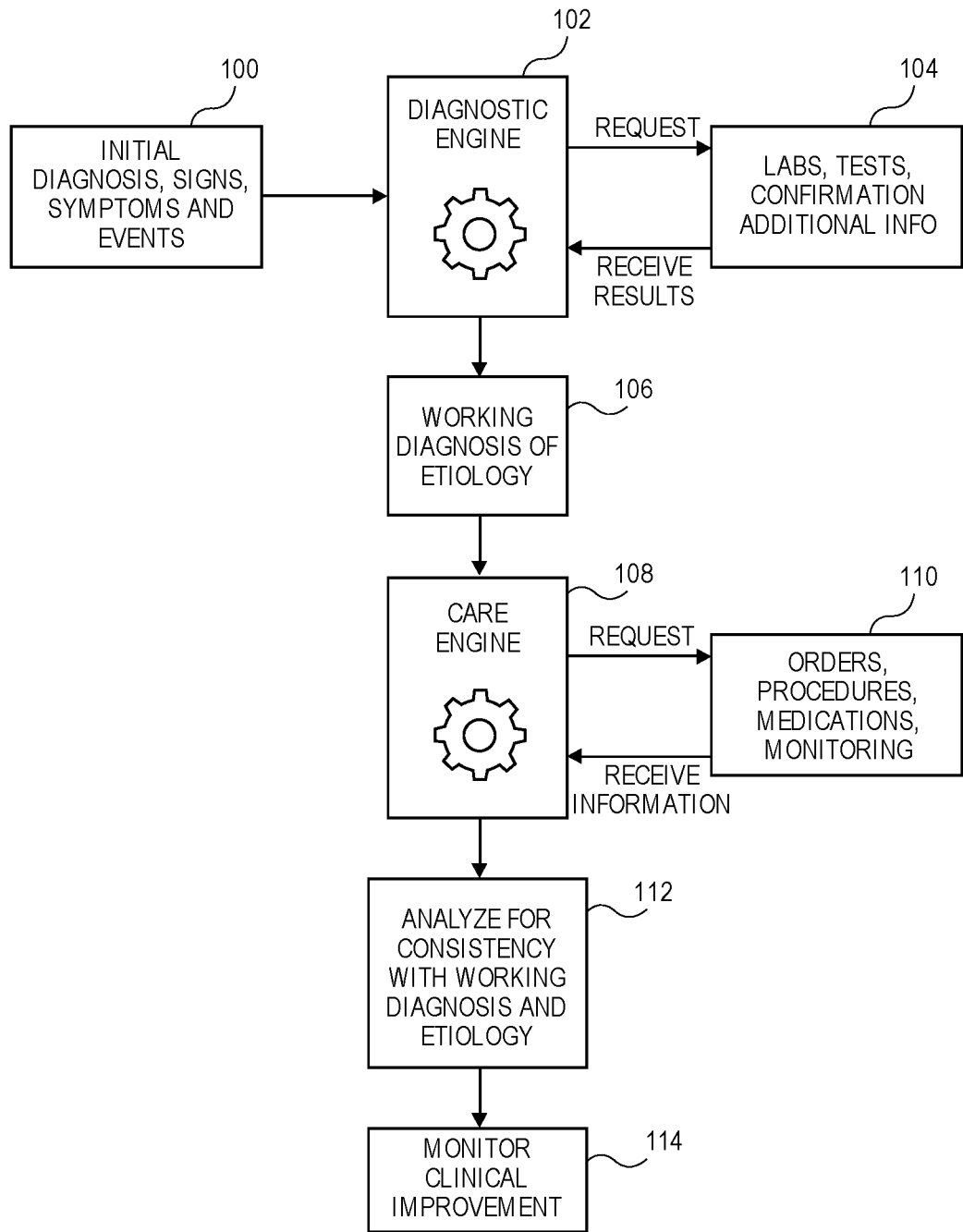
FIG. 1 is a flow diagram illustrating an exemplary diagnostic care coordination system.

The drawing figures do not limit embodiments of the invention to the specific embodiments disclosed and described herein. The drawings are not necessarily to scale, emphasis instead being placed upon clearly illustrating the principles of the invention.

DETAILED DESCRIPTION

The following detailed description references the accompanying drawings that illustrate specific embodiments in which the invention can be practiced. The embodiments are intended to describe aspects of the invention in sufficient detail to enable those skilled in the art to practice the invention. Other embodiments can be utilized and changes can be made without departing from the scope of the invention. The following detailed description is, therefore, not to be taken in a limiting sense. The scope of the invention is defined only by the appended claims, along with the full scope of equivalents to which such claims are entitled.

In this description, references to "one embodiment," "an embodiment," or "embodiments" mean that the feature or features being referred to are included in at least one embodiment of the technology. Separate references to "one embodiment," "an embodiment," or "embodiments" in this description do not necessarily refer to the same embodiment and are also not mutually exclusive unless so stated and/or except as will be readily apparent to those skilled in the art from the description. For example, a feature, structure, act, etc. described in one embodiment may also be included in other embodiments, but is not necessarily included. Thus, the current technology can include a variety of combinations and/or integrations of the embodiments described herein.

The invention provides various embodiments of a computer program, a method, and a system for assisting a caregiver in diagnosing and treating a patient. FIG. 1 illustrates an exemplary diagnostic care coordination system. Broadly, the diagnostic care coordination system comprises a diagnostic engine and a care engine. The diagnostic care coordination system assists a caregiver in diagnosing the patient, determining an etiology of the diagnosis, establishing a treatment plant for the patient, overseeing the administration of the treatment program, assisting in the ongoing monitoring the patient to ensure that the patient's response to the treatment program is consistent with the diagnosis, and (if not) refining the diagnosis and creating a new treatment program.

In Step 100, an initial diagnosis, signs, symptoms, events, and the like are input into the diagnostic engine. This may be in the form of responses to inquiries by the diagnostic engine 102, the input of information via natural language, and the like. The diagnosing engine processes the input information and requests additional information from the user. In this way, the diagnostic engine can eliminate potential diagnoses and classifications of diagnoses.

In some embodiments of the invention, the diagnostic engine comprises a static diagnosing web and a dynamic diagnosing analyzer. The static diagnosing web contains information related to various diagnoses or classes of diagnoses. The dynamic diagnosing analyzer navigates the user through the static diagnosing web so as to request information from the user. This allows the dynamic diagnosing analyzer to come to a proper diagnosis for the patient. The dynamic diagnosing analyzer and the static diagnosing web are discussed in much more depth below.

Depending on the information input into the diagnostic engine, in Step 104 the diagnostic engine requests various labs, tests, confirmations, and additional information. These labs and tests allow the diagnostic engine to have more information from which to diagnose the patient. The confirmations and additional information may be asking a repetitive question to ensure consistent answers, demographic information, patient history information, and the like. The results of these requests are then put into the diagnostic engine. This can take place in numerous cycles based upon the received results and the patient having more than one active disease or condition. Further, the diagnostic engine may ascribe a time stamp to each request and received result. This assists in record keeping and billing, as discussed below.

In Step 106, the diagnostic engine suggests a working diagnosis. The working diagnosis may include a working etiology that is indicative of the causation or origination of the working diagnosis for that patient. The user is requested to take confirmation actions, which may include physiological readings, labs or tests requiring additional input to the working diagnosis. The diagnosis in Step 106 is a "working diagnosis" because the diagnostic engine has sufficiently tested and the user has confirmed the diagnosis such that treatment of the condition can begin. The working diagnosis may be further refined or changed, as discussed below. It should be appreciated that the diagnostic engine is a tool that assists the caregiver in arriving at the working diagnosis and the treatment plan. The diagnostic engine does not overrule the discretion and training of the caregiver, but instead supplements that training in an efficient manner.

In Step 108, the care engine suggests a treatment plan for the patient based upon the working diagnosis. The treatment plan may be based upon the working diagnosis, the working etiology, a patient history, physical characteristics of the patient, available medication and equipment at the care facility, medical review board standards for the working diagnosis for the specific institution, etc. The treatment plan may also be refined or changed based upon the independent judgment of the physician. In Step 110, the care engine suggests orders, procedures, medications, and monitoring based upon the treatment plan. These suggestions are consistent with the treatment plan. The user, observing the suggestions, performs or orders the various task to be performed. The user also inputs an indication of the task being performed along with any quantitative results into the care engine.

Based upon the received information in Step 110, in Step 112, the care engine analyzes the information to determine if the patient reactions and condition are consistent with the working diagnosis and the working etiology. Inconsistencies can be indicative of the working diagnosis and/or the working etiology being incorrect. Inconsistencies can also be indicative of an additional condition, disease, or injury affecting the patient. Inconsistencies could also be indicative of the treatment plan being inappropriate for various reasons (such as an allergic reaction to medication) such that a revised treatment plan is needed. If an inconsistency is found in Step 112, the care engine will determine the basis of the inconsistency and take appropriate action (such as sending information to the diagnostic engine for a revised diagnosis).

If, in Step 112 the care engine determines that the patient reactions and condition are consistent with the working diagnosis, in Step 114, the care engine will continue to provide timely alerts for the monitoring of clinical improvement and oversee the administration of the treatment plan. In some embodiments, the information gathered during the above-discussed steps may be transferred to a record-keeping and/or billing system or department. The record-keeping system or department will retain the information for liability reasons, such that a clear and articulated methodology of the path to diagnosis. Similarly, data for integration to a billing system or department will retain the information to assist in precisely billing the various procedures and tests performed.

Most of this description is broadly directed to the medical field for physician use or under physician supervision, based on the scope, degree and action intrusted in a physician's license, as an exemplary field of use for the invention. It should be appreciated, however, that this is only an exemplary use that should not be construed as limiting on the invention. The medical field is discussed so as to provide a consistent and comprehensible example of embodiments of the invention. In the exemplary field, the patient is a medical patient, the working diagnosis is related to a medical condition of the medical patient, and the treatment plan is a medical treatment plan related to the medical condition of the medical patient.

A few terms relative to the exemplary medical field will be discussed for clarity. As used throughout, "patient" (in the exemplary medical field) means a natural person who has been diagnosed with a disease, who has been injured or wounded, who is recovering from surgery or other operation, or who has other medical needs. The patient need not be under the active treatment of a physician or nurse. For example, embodiments of the invention may be configured for remote diagnosis and care. A patient could also be a person at risk for a disease, injury, or surgery. For example, this could include military personnel at high risk of mental health issues secondary to events experienced in military service, or a person with a strong family history of breast cancer.

As used throughout, "caregiver" (in the exemplary medical field) means any person performing, in at least some capacity, the function diagnosing, treating, assisting, or aiding the patient with their treatment plan. The caregiver may have some amount of medical, nursing, chiropractic, physical therapy, emergency medical, or related training. In some instances, the caregiver may be an assistant of the caregiver so as to record actions taken by the caregiver and provide information from the system to the caregiver. It should also be appreciated that embodiments of the invention assist the caregiver in diagnosing and treating a condition with which the caregiver is unfamiliar. For example, in an emergency situation embodiments of the invention may help a residential nurse quickly determine life saving action and procedure. In this way, the residential nurse can take reasonable action to stabilize the patient or relay information to a doctor upon arrival or transportation to a hospital. In this way, the wealth of knowledge is more readily made available to first responder persons capable of performing such life saving procedures.

As used throughout, "care facility" (in the exemplary medical field) means a medical establishment acting under the supervision and guidance of physician(s) associated with the caregiver to provide tools and facilities for the diagnosis and treatment of the patient. Examples of care facilities include hospitals, doctor offices, residential nursing facilities, and the like.

As used throughout, "diagnosis" (in the exemplary medical field) means the identification of the nature of a certain condition or diseases that is affecting the patient. The diagnosis may be based upon any or all of the following: observations of signs and symptoms of the patient, a review of the patient history, a physical examination of the patient, an administration of diagnostic tests, etc.

As used throughout, "etiology" (in the exemplary medical field) means the causation or origination of the diagnosis. Some diagnoses have numerous possible etiologies. Selecting the correct etiology is therefore important in formulating an effective treatment plan. Similarly, some etiologies present themselves through numerous different diagnoses. In some instances, the diagnosis is determined first, followed by the etiology based upon the possible etiologies for that diagnosis. In other embodiments, the etiology is determined first, followed by the diagnosis based upon possible diagnoses for that etiology. In some instances, the etiology and the diagnosis are determined substantially simultaneously. For example, various etiologies and diagnoses may be considered and eliminated by a single diagnostic test.

As used throughout, "treatment plan" (in the exemplary medical field) means any type of on-going treatment, monitoring, or education. The treatment plan may be regarding medical, nursing, chiropractic, physical therapy, or other related fields. The treatment plan may have hourly, daily, weekly, and/or monthly requirements associated with it. The treatment plan may alternatively or in addition have hourly, daily, weekly, and/or monthly suggestions or recommendations associated with it. A patient may also have multiple treatment plans that cover either a single or multiple diseases or conditions. The treatment plan can also change over time. In some embodiments, the treatment plan has been specifically prescribed or designed for a specific patient. In other embodiments, the treatment plan is generic and could apply to a number of different patients. Examples of treatment plans include monitoring blood sugar for a diabetic patient, monitoring activity level for an elderly patient, providing physical therapy exercises to a patient recovering from an injury, and providing educational materials to a patient recently diagnosed with sickle cell anemia. A treatment plan could also include treatment, monitoring, education, or any combination thereof.

Figure 2:
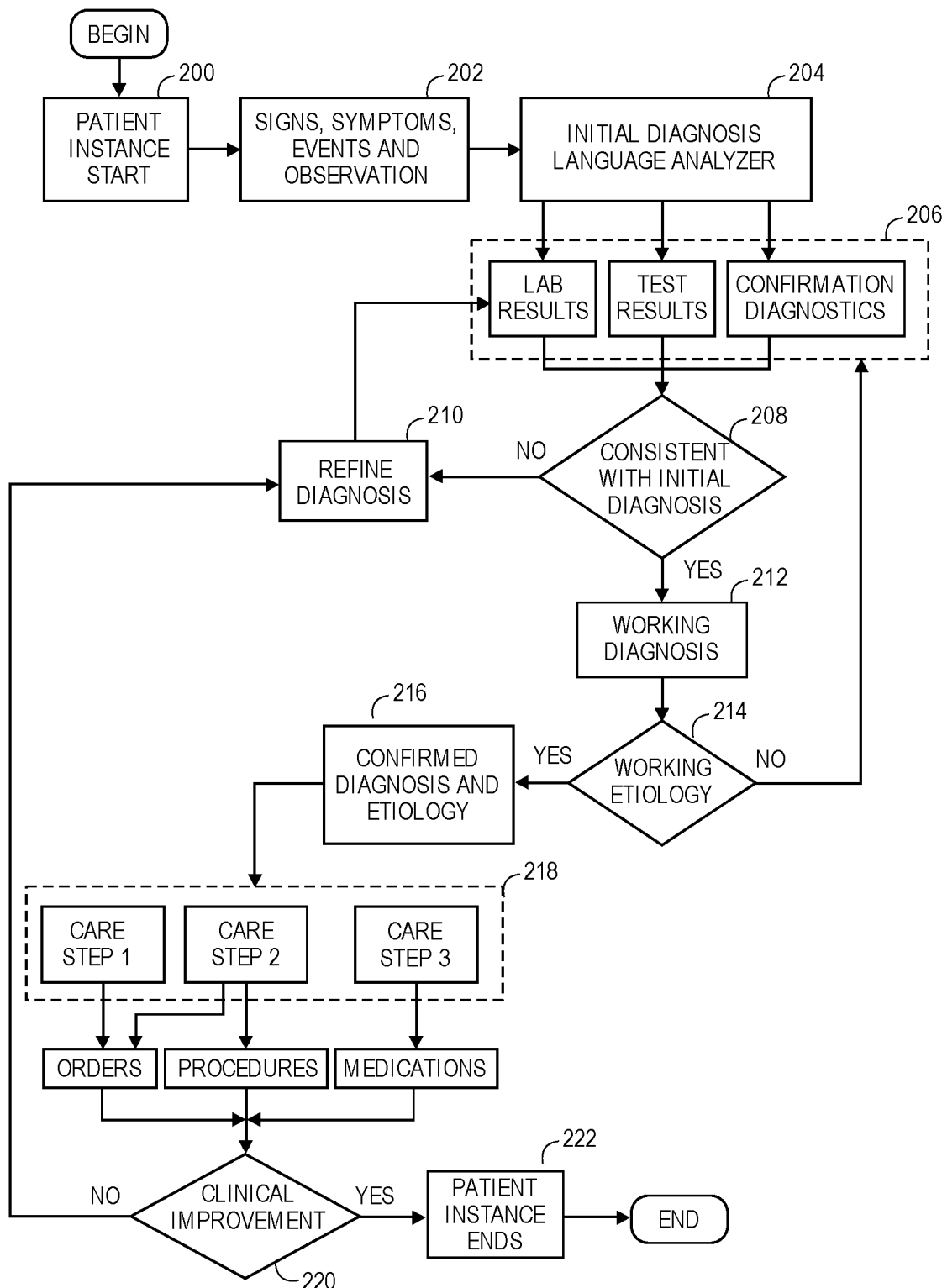
FIG. 2 is a flow diagram illustrating exemplary steps performed by the diagnostic care coordination system.

Returning to the figures, and specifically FIG. 2, a diagnostic care coordination system is shown for assisting with treating a patient. The diagnostic care coordination system is configured to perform various steps and functions to assist a caregiver in diagnosing and treating a patient, or assist in the coordination and handoff of various steps and functions from caregiver to caregiver, while maintaining an accurate stream of action as necessary for medical record keeping and billing. The diagnostic care coordination system is a tool that directs the caregiver toward the correct diagnosis by requesting and suggesting certain diagnostic tests, eliminating certain diagnoses, requesting and suggesting certain care steps, etc.

In Step 200, the patient instance begins. The patient instance is a certain instance relevant to the patient. The instance will follow as the patient is diagnosed and treated. The instance may be passed between caregivers and/or between care facilities. For example, during a shift change, the patient instance may be transferred to a user device associated with the second shift. As another example, if the patient is transferred from an emergency room to an operating room or an intensive care unit, the patient instance is made accessible to user devices associated with the operating room or the intensive care unit such that the new user device has access to the knowledge and decision making process that has taken place thus far. As yet a further example, the patient instance may begin in the patient's home by an emergency medical technician responding to an emergency call. In this way, the hospital has instantaneous access to observations, initial diagnoses, and timestamps for various procedures and medications performed by the emergency medical technician.

In Step 202, signs, symptoms, events, and observations are put into the system by the user. These may be selected from a list, selected by category, input in a text string, input by voice recognition, etc. In Step 204, an initial diagnosis is input or calculated by the dynamic diagnosing analyzer based upon the input information. This initial diagnosis may be a categorical diagnosis (such as "renal failure" or "breathing difficulty"). A language analyzer may be used in Step 204 to interpret and categorize the text or voice inputs from the user. For example, the language analyzer may note certain keywords or phrases input and use these to categorize the diagnosis or to bring the user to to certain starting location on the static diagnosing web.

In Step 206, the dynamic diagnosing analyzer begins to refine and suggest an initial diagnosis, including arriving at an etiology. The dynamic diagnosing analyzer may request certain labs, tests, and diagnostics based upon the information in the static diagnosing web. The lab results, test results, and confirmation diagnostic results are then fed back into the dynamic diagnosing analyzer.

Figure 3:
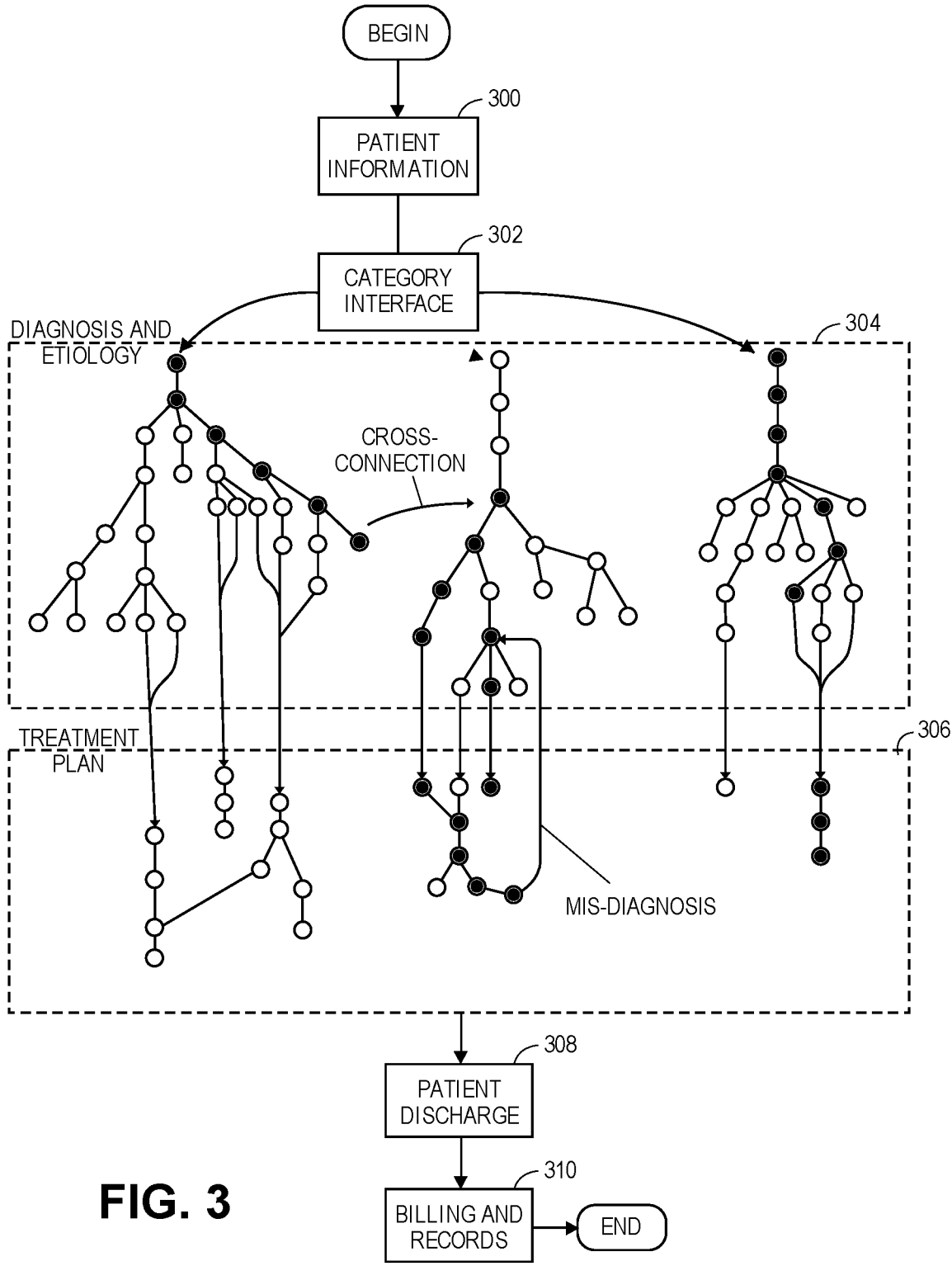
FIG. 3 is a flow diagram illustrating navigation of a dynamic diagnosing analyzer through a static diagnosing web.

In Step 208, the dynamic diagnosing analyzer determines whether the lab results, the test results, and/or the confirmation diagnostic results are consistent with the initial diagnosis. If they are consistent, the dynamic diagnosing analyzer will continue to move through the static diagnosing web (as illustrated in FIG. 3). If they are not consistent, the dynamic diagnosing analyzer may jump to another portion of the static diagnosing web, so as to attempt to confirm another diagnosis. The dynamic diagnosing analyzer therefore analyzes the results to attempt to find one or more potential diagnosis that would be consistent with the results and information received.

In Step 210, the dynamic diagnosing analyzer may refine or completely change the diagnosis based upon the inconsistencies with the initial diagnosis. As discussed above, this may include moving to another portion of the static diagnosing web, moving the user back up the static diagnosing web so as to reconfirm or repeat a test, making a unique and novel connection between information nodes of the static diagnosing web, etc. In some instances, the patient has more than one condition or diagnosis. As such, the patient may have more than one diagnosis, which may cloud or complicate the calculations of the dynamic diagnosing analyzer. The dynamic diagnosing analyzer may therefore move to another portion of the static diagnosing web so as to find additional diagnoses.

In Step 212, as the dynamic diagnosing analyzer is finding consistency with the diagnosis and the test results as discussed in Step 208, the dynamic diagnosing analyzer designates the diagnosis as a working diagnosis and begins to calculate the etiology of the working diagnosis. However, it should be appreciated that in many instances, the determination of a diagnosis is necessarily tied to the determination an etiology for that diagnosis. In arriving at the working diagnosis, the dynamic diagnosing analyzer has, in many instances, eliminated several or all-but-one possible etiologies.

In Step 214, the dynamic diagnosing analyzer refines the etiology. Finding a correct etiology is critical for finding a correct treatment plan to treat the diagnosis. Many or most diagnoses can be caused by any of several underlying causes. You treat for the diagnosis by addressing the underlying cause. This may include requesting additional tests, labs, and the like so as to verify the etiology.

In Step 216, the diagnostic engine determines that it has arrived at a working diagnosis and looks for confirmation from a trained profession, along with the working etiology and sends this to the care engine. The working diagnosis and the working etiology are sufficiently definite so as to determine and begin a treatment plan. It should be noted that in many embodiments, symptom management may be initiated before a working diagnosis has been identified. For example, a high fever may be treated with a fever reducer before the etiology of why the patient has the fever has been fully determined. This is because forgoing preliminary treatments of the patient can exacerbate the patient.

In Step 218, the care engine suggests a treatment plan based upon the working diagnosis and information about the patient. The care engine may be separate and distinct from the diagnostic engine or inter-related. In Step 218, the treatment plan is implemented such that the various care steps (such as orders, procedures, medications, and the like) are requested.

In Step 220, information associated with patient improvement, response, and progress are received by the care engine. Depending on whether the received information is indicative of a clinical improvement that would be expected on a standard patient, the care engine may determine that a misdiagnosis or a incomplete diagnosis was provided by the diagnosing engine. As such, the care engine may send information back to the diagnosing engine such that a refined diagnosis can be determined. In other embodiments, the information about patient response is automatically sent to the diagnosing engine and the diagnosing engine determines whether clinical improvement is progressing as expected.

If clinical improvement is observed and the treatment plan is completed, in Step 222 the patient instance ends. This can include a transfer of the patient information to a billing and/or record keeping system, as discussed above. This may also include a transfer of patient care to a caregiver outside the system.

FIG. 3 illustrates another embodiment of the invention. FIG. 3 more clearly illustrates an example of the static diagnosing web and how the dynamic diagnosing analyzer navigates the user through the static diagnosing web. The diagnostic engine illustrated in FIG. 3 generates a working diagnosis of the patient. The working diagnosis includes a working etiology indicative of a cause or source of the working diagnosis. The treatment plan is associated with the working etiology and the working diagnosis.

Illustrated in FIG. 3 is an exemplary representation of the static diagnosing web containing a plurality of information nodes. Each information node includes information related to a diagnosis and/or an etiology. Certain (or all) information nodes will include an inquiry, question, information field, or the like. Based upon the response to the inquiry, question, information field, or the like, the dynamic diagnosing analyzer will determine to which information node to continue. Examples of the information nodes will be shown and discussed in regards to FIG. 4.

In Step 300, the diagnostic engine receives patient information associated with the patient. The patient information may include a patient identifier, patient characteristics, patient signs and symptoms, or other information related to the patient. Examples of patient information include name, social security number, a patient identification number, patient demographical information, patient physical characteristics, patient medical history, or similar information. In some instances, the user may not know any patient information or time pressure prevents the entering of patient information. In these instances the system may assign a patient identification number, such that the patient identification number may later be correlated or otherwise associated with the patient name. In some embodiments, a patient identification number is used throughout the system so as to alleviate privacy concerns based upon later analysis and adaptation of the information in future iterations of the system. The patient identification number may be later associated with the patient name and other information, such as for record-keeping and billing purposes.

Figures 4A, 4B:
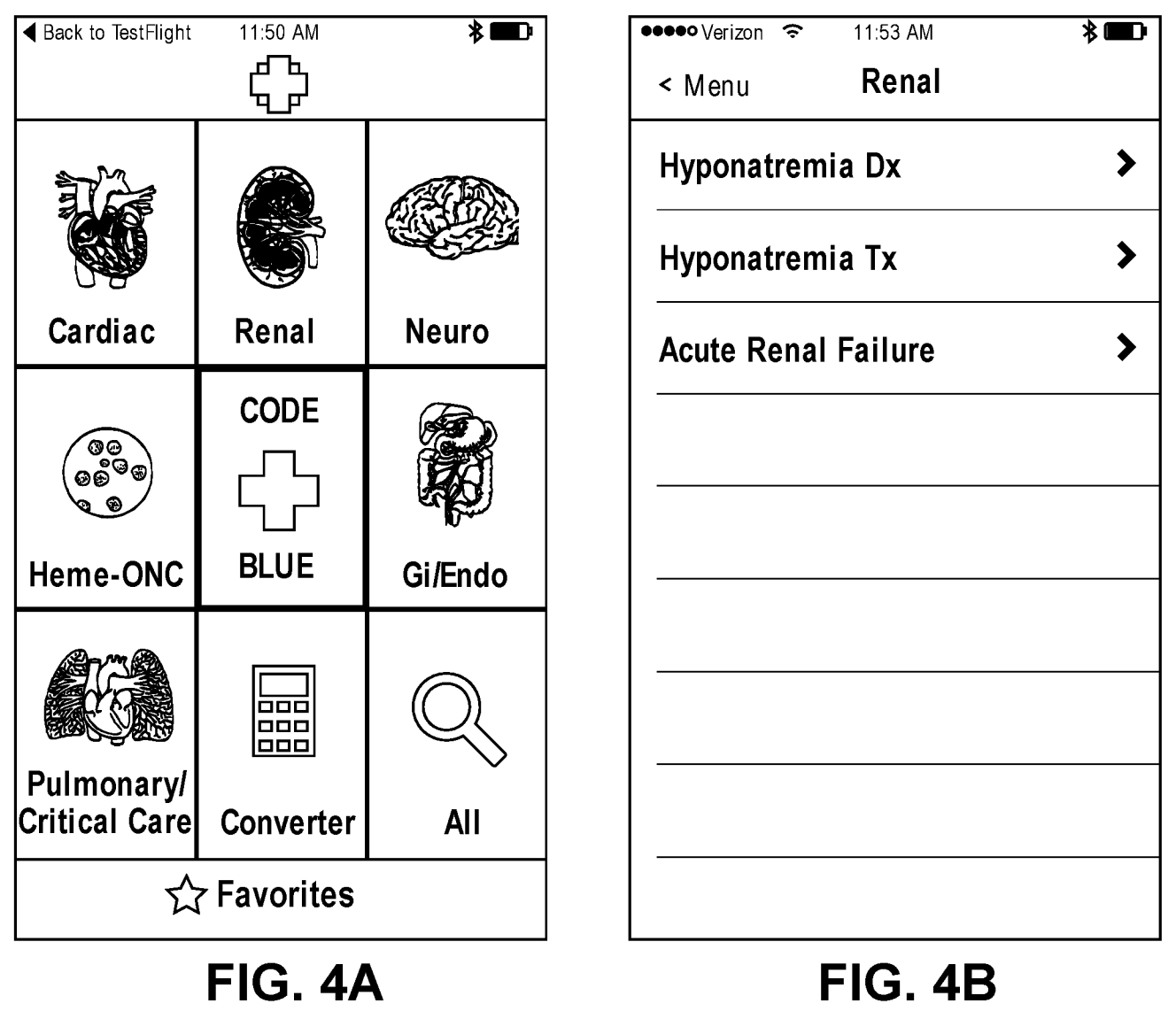

In Step 302, the system presents a category interface to the user (such as illustrated in FIG. 4A). The category interface allows the user to select a category, specialty, or location in which to begin the diagnosing process. The category selected may be based on signs and symptoms presented by the user, an initial diagnosis that the caregiver suspects is affecting the patient, patient characteristics or other considerations. The category interface may also include sub-category interfaces. A sub-category interface presents possible diagnoses, symptoms, or specialties within that categories (as illustrated in FIG. 4B). In some embodiments of the invention, the category interface may additionally or alternatively include a textual or language input and a language analyzer. The language analyzer may select a category and/or an initial diagnosis based upon an analysis of the input text or language from the user.

In Step 304, the dynamic diagnosing analyzer presents to the user a plurality of information requests. The dynamic diagnosing analyzer navigates a user through the plurality of information nodes of the static diagnosing web based upon received responses to the plurality of information requests.

Based upon a route through the static diagnosing web as taken by the dynamic diagnosing analyzer, the diagnostic engine generates the working diagnosis. A simplified example of the navigation is illustrated in FIG. 3. Starting on the top-left of the box denoted 304 (which may be the first information node within the category interface or the sub-category interface), the dynamic diagnosing analyzer presents the information requests to the user. The information requests inquire as to information about the patient and requests tests, labs, and other confirmation diagnostics be performed. As can be seen in Step 304, certain information nodes proceed linearly, certain information nodes branch outward, and certain information nodes branch inward.

It should be appreciated that in certain embodiments of the invention, the static diagnosing web is fixed and the dynamic diagnosing analyzer chooses a unique route through those information nodes. For example, following many iterations of the system, the dynamic diagnosing analyzer may determine that a certain etiology for a certain diagnosis is very common. As such, the dynamic diagnosing analyzer may present information requests associated with that etiology sooner. This may increase the speed to diagnosis and allow the dynamic diagnosing analyzer to arrive at the correct diagnosis with fewer diagnostic tests performed. The dynamic diagnosing analyzer may therefore become more proficient and efficient at detecting patterns and deducing diagnoses than any human could become. This artificial intelligence may also allow the dynamic diagnosing analyzer to predict the outcomes of various diagnostic tests. For example, say that a certain diagnosis has five known etiologies. Based upon historical iterations involving similar patients and known medical frequencies, the dynamic diagnosing analyzer may determine the relative likelihood of each etiology. The dynamic diagnosing analyzer may then select or eliminate etiologies in the most efficient manner. The selection may be based upon the likelihood of the etiology, the time and expense of the diagnostic test, etiological overlap of the tests, the likelihood of a false positive or a false negative for the diagnostic test, and other considerations.

In some instances, the dynamic diagnosing analyzer may determine that the path being navigated is inconsistent or that another diagnosis may additionally or alternatively explain the signs and symptoms being input. In these instances, the dynamic diagnosing analyzer may move via a cross-connection to a new position in the static diagnosing web. The cross-connection is a link between two information nodes that are not otherwise connected. Other examples of cross-connections could be to diagnose two or more concurrent conditions, to quickly eliminate a potential additional diagnosis, to skip or reorder information nodes that are less likely to lead to the correct diagnosis, etc. In some instances the dynamic diagnosing analyzer navigates the user through otherwise unrelated information nodes so as to arrive at a first diagnosis and a second diagnosis. As such, the dynamic diagnosing analyzer may move between these unrelated information nodes so as to diagnose both the first diagnosis and the second diagnosis substantially simultaneously.

In some embodiments, the diagnostic engine is configured to receive an initial diagnosis from the user. The dynamic diagnosing analyzer moves the user to a specific location based upon the initial diagnosis. The language analyzer determines the initial diagnosis based upon an input from the user. For example, as illustrated on the right side of the box labeled 304, the language analyzer may redirect the dynamic diagnosing analyzer to a secondary position on the static diagnosing web. The language analyzer may operate before, during, or after the diagnosis to the first diagnosis. The analysis attempts to determine patterns and structure to the unstructured inputs from the user. The system may perform an initial analysis of the transcript by the vectorization of term frequencies and term frequency inverse document frequency. These vectorizations identify important words (or the root words thereof) and their frequency. The vectorizations may also identify words that may be keywords that may be associated with a certain diagnosis or category of diagnoses. The system may then determine the appropriate starting node by various methods such as latent semantic indexing, latent dirichlet allocation, and non-negative matrix factorization.

In embodiments of the invention, the dynamic diagnosing analyzer records the received responses and assigns a timestamp to at least one of the received responses. The timestamps provide a timed map to demonstrate how, when, and why the caregiver arrived at the diagnosis. This can be beneficial for any of several reasons. First, the timestamps can provide continuity as the patient passes between caregivers and/or care facilities. For example, at a shift change, the new shift can know exactly when various procedures were performed and observe how the former shift arrived at the diagnosis. This can allow the new shift to avoid duplicative tests and procedures, continue the diagnostic process, or oversee the treatment plan. Second, the timestamps provide a secure and accurate record of the steps and procedures performed. This can be beneficial in the case of litigation, such that the caregiver can easily and credibly demonstrate the diagnostic and care processes.

In Step 306, the care engine determines a treatment plan based upon the working diagnosis. The treatment plan includes a set of care steps that are to be performed so as to treat, manage, or cure the working diagnosis and/or the working etiology. In embodiments of the invention, such as illustrated in FIG. 3, the treatment plan may be based upon information nodes that follow from the static diagnosing web. In some embodiments, the treatment plan is a component of the static diagnosing web, as shown in FIG. 3.

In embodiments of the invention the treatment plan is a single comprehensive treatment plan configured to address the first diagnosis and the second diagnosis. The set of care steps associated with the comprehensive treatment plan prevents or reduces redundant care steps that would be present in a first treatment plan for the first diagnosis and a second treatment plan for the second diagnosis. For example, a first diagnosis may require blood tests every three days and a second diagnosis may require blood tests once per week. The treatment plan may therefore only require a blood test every three days, so as to prevent duplicative blood tests. As another example, a first medication is used to treat a first diagnosis and a second medication is used to treat a second diagnosis. The care engine knows that the first medication interferes with the second medication. As such, the care engine may recommend the first medication and a third medication (which also treats the second diagnosis) so as to avoid the interference.

The care engine oversees administration of the set of care steps to determine whether a patient response to the treatment plan is consistent with the working diagnosis. As can be seen toward the center of the box labeled 306, the care engine may determine that a mis-diagnosis has occurred. As such, the care engine may send information back up to the diagnostic engine for a re-diagnosis. The diagnostic engine may then select an information node to which to restart the diagnostic process, as illustrated at the bottom of box 304. A successful re-diagnosis by the diagnostic engine will then return to the care engine via a different treatment plan.

In Step 308, upon the patient showing clinical improvement, the patient is discharged and the patient instance is completed. In some instances the patient may be discharged from the system prior to the patient being discharged from the care facility. Similarly, the patient may be transferred to another care facility (as discussed below) for follow-on treatments. The patient may be discharged from the system upon the patient showing sufficient clinical improvement so as to verify the working diagnosis and the working etiology.

In Step 310, information from the system is provided to billing and records. In embodiments of the invention the diagnostic engine provides the received responses and the timestamps to a records engine to facilitate record keeping and billing associated with the patient. In some embodiments, information nodes are associated with various billing codes so as to facilitate the billing for services. For example, medical billing of the prior art is a time- and work-intensive process to determine exactly what procedures the caregiver performed based upon later-created notes. Embodiments of the invention reduce this burden by automatically associating a billing code (or a unique code indicative of a billing code) with the information node and the time stamp. This information may be associated with the patient information, added to the patient history, added to a patient account, added to a repository for future analytics, or otherwise stored.

In embodiments of the invention, the system supports efficient transfer of the patient between users. In embodiments of the invention, the user is a first user having a first specialty. The diagnostic engine is configured to transfer operations to a second user having a second specialty. Based upon the active user, the dynamic diagnosing analyzer presents the plurality of information requests related to the first or second specialty. In this way, the dynamic diagnosing analyzer adapts to the current user so as to facilitate diagnosis and care. Similarly, the dynamic diagnosing analyzer can notify the user that another user has completed certain tasks or that the other user is needed to perform certain tasks. For example, if the second user is a surgeon and the first user is a nurse practitioner, the system may notify the nurse practitioner of the post-operative care required to care for the patient following surgery. Similarly, the system may inform the surgeon (or associated person) of specific care steps that should be accomplished as part of the surgery.

In embodiments of the invention, the first user is associated with a first care facility and the second user is associated with a second care facility that is different than the first care facility. The first care facility and the second care facility may be associated with the same hospital or network of hospitals. For example, the first care facility may be an emergency room and the second care facility may be an intensive care unit of a single hospital. As another example, the first care facility may be a hospital and the second care facility may be a residential nursing facility. By transferring the user between care facilities, the system allows the various care facilities to observe, track, and understand the diagnostic and care procedures that have been performed. For example, the residential nursing facility may be able to see how and why the patient was diagnosed so as to assist the residential nursing facility with caring for the patient.

FIG. 4 illustrates an exemplary navigation of the dynamic diagnosing analyzer through the static diagnosing web. It should be appreciated that FIG. 4 is provided to give the reader an appreciation for an exemplary way of utilizing and presenting an embodiment of the invention.

FIG. 4A illustrates an exemplary category interface, such as was discussed in regards to Step 302. The category interface may present to the user options such that the user can select a category of a suspected initial diagnosis. For example, if the patient presents with gastro-intestinal pain, the user may select the Gi/Endo button presented. As another example, if the patient has stopped breathing, the user may select the code blue button which will assist the user in rapidly reviving the patient. It should be appreciated that in some embodiments, the category interface is optional for users that have an initial category of diagnosis in mind. In other embodiments, the user may be presented with a listing of possible symptoms to select, a textual or voice input, patient information requests, or the like.

FIG. 4B illustrates an exemplary sub-category interface of the renal category, such as was also discussed in regards to Step 302. The sub-category interface allows the users to select a sub-category of diagnosis if such is known or suspected. It should be appreciated that the dynamic diagnosing analyzer is configured to identify and correct initial mis-diagnoses. The subcategory interface allows a shortcut for the user if desired.

FIG. 4C illustrates an exemplary information request presented to the user in regards to an exemplary hyponatremia diagnosis. Based upon the user selection, the dynamic diagnosing analyzer begins the analysis at a hyponatremia information node. The dynamic diagnosing analyzer the requests from the user certain information with regards to the patient. For example, as illustrated, the dynamic diagnosing analyzer may request a patient range of serum osmolality. Serum osmolality is an amount of chemicals (such as sodium) dissolved in the liquid part (serum) of the blood. It should be noted that in embodiments of the invention, the dynamic diagnosing analyzer requests and presents ranges for input. The ranges may be advantageous for speed of entry.

FIG. 4D illustrates an exemplary dropdown menu from the "volume status" entry field of FIG. 4C. The dropdown menu may be presented on an entire screen, as shown, so as to provide additional information to the user. The entire screen also allows for quick and accurate selection. Upon the selection by the user, the dynamic diagnosing analyzer may return the user to the screen of FIG. 4C.

FIGS. 4E and 4F illustrate an exemplary information request presented to the user. These views illustrate embodiments of the invention in which relevant information is presented to the user to help guide the user in correctly diagnosing and treating the patient. The user then provides feedback to the system so as to help guide the dynamic diagnosing analyzer to arrive at the correct diagnosis. This can include information on how and when to treat the symptoms described, what further information is needed, and the like.

FIGS. 4G and 4H illustrate an exemplary information requested by the care engine. The care engine may request additional information such that the treatment plan can be accurately, precisely, and correctly formulated for the patient. For example, the care engine may ask the gender and general age of the patient. Such information was unimportant when coming to the diagnosis and the etiology, but becomes important in formulating a proper treatment plan. The age and gender of the patient may be indicative of a proper medication level and frequency. As another example, the care engine may request information as to the effectiveness of the treatments and symptom suppressions that have been performed thus far. The patient progress thus far is also indicative of the various care steps of the treatment plan.

FIG. 4I illustrates an exemplary treatment plan for hyponatremia that is tailored to a specific patient given a specific set of information regarding the patient. The treatment plan includes instructions, care steps, goals, and the like. For example, the treatment plan provides for an infusion rate of 73.1 mL/hr for the first four hours, followed by an infusion rate of 131.5 mL/hr for the last twenty hours of a twenty-four hour treatment plan. It should be appreciated that these exemplary numbers provide a precision in calculation which is not possible under The treatment plan may also allow for the input of information regarding the successfulness of the treatment plan. As such, inconsistencies can be addressed by either altering the treatment plan or arriving at a revised diagnosis.

Figure 5:
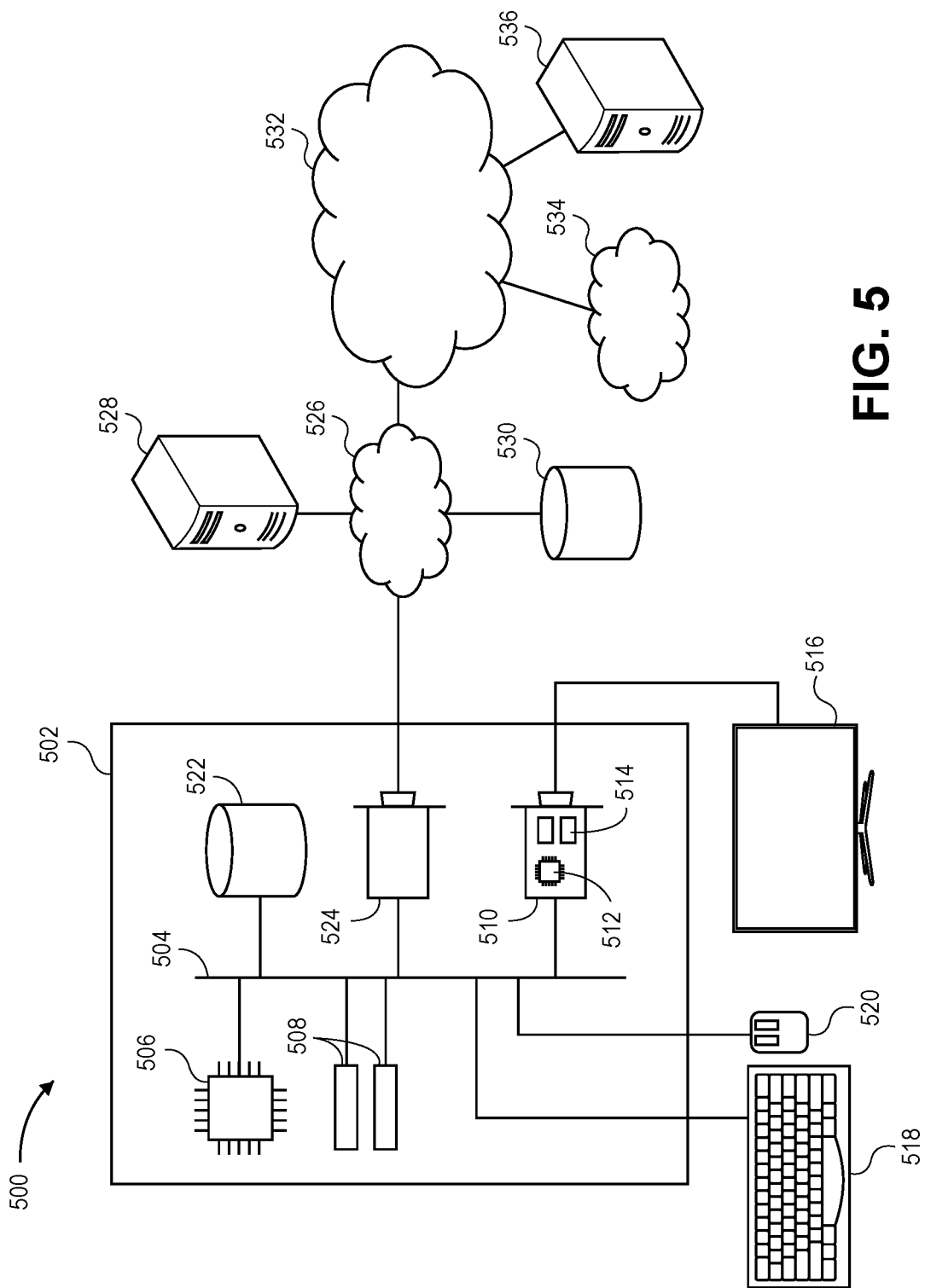
FIG. 5 is a system diagram illustrating the various hardware components of embodiments of the invention.

Turning to FIG. 5, the physical hardware that makes up the system will now be discussed. The system 500 comprising an exemplary hardware platform that can form one element of certain embodiments of the invention is depicted. Computer 502 can be a desktop computer, a laptop computer, a server computer, a mobile device such as a smartphone or tablet, or any other form factor of general- or special-purpose computing device. Depicted with computer 502 are several components, for illustrative purposes. In some embodiments, certain components may be arranged differently or absent. Additional components may also be present. Included in computer 502 is system bus 504, whereby other components of computer 502 can communicate with each other. In certain embodiments, there may be multiple busses or components may communicate with each other directly. Connected to system bus 504 is central processing unit (CPU) 506. Also attached to system bus 504 are one or more random-access memory (RAM) modules 508.

Also attached to system bus 504 is graphics card 510. In some embodiments, graphics card 510 may not be a physically separate card, but rather may be integrated into the motherboard or the CPU 506. In some embodiments, graphics card 510 has a separate graphics-processing unit (GPU) 512, which can be used for graphics processing or for general purpose computing (GPGPU). Also on graphics card 510 is GPU memory 514. Connected (directly or indirectly) to graphics card 510 is display 516 for user interaction. In some embodiments no display is present, while in others it is integrated into computer 502. Similarly, peripherals such as keyboard 518 and mouse 520 are connected to system bus 504. Like display 516, these peripherals may be integrated into computer 502 or absent. Also connected to system bus 504 is local storage 522, which may be any form of computer-readable media, and may be internally installed in computer 502 or externally and removably attached.

Finally, network interface card (NIC) 524 is also attached to system bus 504 and allows computer 502 to communicate over a network such as network 526. NIC 524 can be any form of network interface known in the art, such as Ethernet, ATM, fiber, Bluetooth, or Wi-Fi (i.e., the IEEE 802.11 family of standards). NIC 524 connects computer 502 to local network 526, which may also include one or more other computers, such as computer 528, and network storage, such as data store 530. Local network 526 is in turn connected to Internet 532, which connects many networks such as local network 526, remote network 534 or directly attached computers such as computer 536. In some embodiments, computer 502 can itself be directly connected to Internet 532.

The computer program of embodiments of the invention comprises a plurality of code segments executable by a computing device for performing the steps of various methods of the invention. The steps of the method may be performed in the order described, or they may be performed in a different order, unless otherwise expressly stated. Furthermore, some steps may be performed concurrently as opposed to sequentially. Also, some steps may be optional. The computer program may also execute additional steps not described herein. The computer program, system, and method of embodiments of the invention may be implemented in hardware, software, firmware, or combinations thereof using a user engagement system, which broadly comprises server devices, computing devices, and a communications network.

The computer program of embodiments of the invention may be responsive to user input. As defined herein user input may be received from a variety of computing devices including but not limited to the following: desktops, laptops, calculators, telephones, smartphones, or tablets. The computing devices may receive user input from a variety of sources including but not limited to the following: keyboards, keypads, mice, trackpads, trackballs, pen-input devices, printers, scanners, facsimile, touchscreens, network transmissions, verbal/vocal commands, gestures, button presses or the like.

The server devices and computing devices may include any device, component, or equipment with a processing element and associated memory elements. The processing element may implement operating systems, and may be capable of executing the computer program, which is also generally known as instructions, commands, software code, executables, applications ("apps"), and the like. The processing element may include processors, microprocessors, microcontrollers, field programmable gate arrays, and the like, or combinations thereof. The memory elements may be capable of storing or retaining the computer program and may also store data, typically binary data, including text, databases, graphics, audio, video, combinations thereof, and the like. The memory elements may also be known as a "computer-readable storage medium" and may include random access memory (RAM), read only memory (ROM), flash drive memory, floppy disks, hard disk drives, optical storage media such as compact discs (CDs or CDROMs), digital video disc (DVD), and the like, or combinations thereof. In addition to these memory elements, the server devices may further include file stores comprising a plurality of hard disk drives, network attached storage, or a separate storage network.

The computing devices may specifically include mobile communication devices (including wireless devices), work stations, desktop computers, laptop computers, palmtop computers, tablet computers, portable digital assistants (PDA), smart phones, smart watches, other smart wearables, and the like, or combinations thereof. Various embodiments of the computing device may also include voice communication devices, such as cell phones and/or smart phones. In some embodiments, the computing device will have an electronic display operable to display visual graphics, images, text, etc. In certain embodiments, the computer program facilitates interaction and communication through a graphical user interface (GUI) that is displayed via the electronic display. The GUI enables the user to interact with the electronic display by touching or pointing at display areas to provide information to the system.

The communications network may be wired or wireless and may include servers, routers, switches, wireless receivers and transmitters, and the like, as well as electrically conductive cables or optical cables. The communications network may also include local, metro, or wide area networks, as well as the Internet, or other cloud networks. Furthermore, the communications network may include cellular or mobile phone networks, as well as landline phone networks, public switched telephone networks, fiber optic networks, or the like.

The computer program may run on computing devices or, alternatively, may run on one or more server devices. In certain embodiments of the invention, the computer program may be embodied in a stand-alone computer program (i.e., an "app") downloaded on a user's computing device or in a web-accessible program that is accessible by the user's computing device via the communications network. As used herein, the stand-alone computer program or web-accessible program provides users with access to an electronic resource from which the users can interact with various embodiments of the invention.

In embodiments of the invention users may be provided with different types of accounts. Each type of user account may provide their respective users with unique roles, capabilities, and permissions with respect to implementing embodiments of the invention. For instance, a caregiver may be provided with a caregiver account that permits the caregiver to access embodiments of the invention that are applicable to the diagnosis and treatment of multiple patients. Additionally, care facility administrators may be provided with an administrator account that permits administrator to monitor and record activities performed by the caregiver on behalf of the patient. Additionally, the patient may be provided with a patient account that permits the patient to review and understand their diagnosis, etiology, and treatment plan. In addition, any number and/or any specific types of accounts is provided as may be necessary to carry out the functions, features, and/or implementations of the invention. Upon a caregiver, administrator, or patient logging in to the electronic resource for a first time, the caregiver, administrator, or patient may be required to provide various items of identification information to create their respective accounts. Such identification information may include, for instance, personal name, business name, email address, phone number, or the like. Upon providing the identification information, the user may be required to enter (or may be given) a username and password, which will be required to access the electronic resource.

Execution of the computer program of embodiments of the invention performs steps of the method of embodiments of the invention. Because multiple users may be updating information stored, displayed, and acted upon by the computer program, information displayed by the computer program is displayed in real-time. "Real-time" as defined herein is when the processing element of the system 500 performs the steps less than every 1 second, every 500 milliseconds, every 100 milliseconds, or every 16 milliseconds.

The method of embodiments of the invention for providing the GUI broadly comprises the following steps: accepting user input, updating information in response to user input, providing an updated GUI. Initialization of the computer program by a user, as may occur when a new user begins to use the system, includes the following additional steps: prompting for the user login, retrieving the credentials input by the user, and determining the first screen of the GUI to provide to the user. Additional steps are also performed if the user has never used the system before, namely prompting the user to create a login and verifying the login is available.

The method of embodiments of the invention for providing the secondary GUI broadly comprises the following steps: accepting user input, updating information in response to user input, and providing an updated GUI. Each time the user opens the computer program comprises the following additional steps: verifying the credentials of the user, determining the first screen of the GUI to provide to the user. The secondary GUI is deployed in response to the message sent to the user so creating a login does not need to be performed.

Although embodiments of the invention have been described with reference to the embodiments illustrated in the attached drawing figures, it is noted that equivalents may be employed and substitutions made herein without departing from the scope of the invention as recited in the claims.

Having thus described various embodiments of the invention, what is claimed as new and desired to be protected by Letters Patent includes the following:

1. A computerized method for providing a diagnosis of a patient during a patient instance comprising:
   presenting to a user a plurality of information requests related to the patient instance, including symptoms and events,
   collecting a plurality of responses from the user to said plurality of information requests,
   directing the user through a plurality of information nodes of a static diagnosing web based upon the received plurality of responses,
   suggesting an initial working diagnosis of a patient to the user via a diagnostic engine based upon a route through the static diagnosing web;
   suggesting an initial treatment plan for the patient via a care engine based upon said initial working diagnosis,
   wherein the initial treatment plan includes a plurality of care steps,
   wherein the initial working diagnosis includes a plurality of working etiologies,
   wherein a relative likelihood of each working etiology of the plurality of working etiologies is determined by a processing unit based at least in part on a comparison of the patient instance to historical patient instances involving other similarly situated patients; and
   refining the initial working diagnosis based upon additional input from the user.

2. The computerized method of claim 1, further comprising:
   suggesting the initial treatment plan based on the relative likelihoods of the plurality of working etiologies.

3. The computerized method of claim 1, further comprising:
   receiving a preliminary diagnosis from the user before the step of presenting the user with a plurality of information requests; and
   directing the user to a specific location in the static diagnosing web based upon the preliminary diagnosis.

4. The computerized method of claim 3, further comprising:
   providing unstructured inputs to a language analyzer from the user; and
   determining the initial diagnosis from the unstructured inputs.

5. The computerized method of claim 1, further comprising:
   assigning a timestamp to at least one of said received responses.

6. The computerized method of claim 5, further comprising:
   using one or more of said assigned timestamps to facilitate record keeping and billing associated with the patient.

7. The computerized method of claim 1,
   wherein said initial working diagnosis includes a first diagnosis related to the patient and a second diagnosis related to the patient.

8. The computerized method of claim 7, further comprising:
   creating a single comprehensive treatment plan configured to treat the first diagnosis and the second diagnosis,
   generating a set of care steps associated with said comprehensive treatment plan by consolidating redundant care steps present in both the first treatment plan for the first diagnosis and the second treatment plan for the second diagnosis.

9. The computerized method of claim 7, further comprising:
   concurrently navigating the user through otherwise unrelated information nodes so as to arrive at the first diagnosis and the second diagnosis.

10. The computerized method of claim 1, wherein the user is a first user having a first specialty, further comprising:
    transferring operations to a second user having a second specialty,
    presenting said plurality of information requests related to the second specialty in response to said transfer of operations to the second user.

11. The computerized method of claim 10,
    wherein the first user is associated with a first care facility,
    wherein the second user is associated with a second care facility that is different than the first care facility,
    wherein said step of transferring operations to the second user is performed in response to the patient being moved from the first care facility to the second care facility.

12. A system for assisting with treating a patient by providing a diagnosis of a patient during a patient instance, the system comprising:
    a non-transitory computer readable storage media having a computer program stored thereon, wherein the computer program instructs at least one processing element to perform the following steps:
    presenting to a user a plurality of information requests related to the patient instance, including symptoms and events;
    collecting a plurality of responses from the user to said plurality of information requests;
    navigating the user through a plurality of information nodes of a static diagnosing web based upon the plurality of received responses from said plurality of information requests; and
    suggesting a first working diagnosis of a patient to the user via a diagnostic engine based at least in part upon a route through the static diagnosing web,
    suggesting an initial treatment plan for the patient via a care engine based upon said first working diagnosis,
    wherein the initial treatment plan includes a plurality of care steps,
    wherein the first working diagnosis includes a plurality of working etiologies indicative of a cause of the first working diagnosis, and
    wherein a relative likelihood of each working etiology of the plurality of working etiologies is determined by the at least one processing element based at least in part on a comparison of the patient instance to historical patient instances involving other similarly situated patients; and
    refining the first working diagnosis based upon additional input from the user.

13. The system of claim 12, further comprising:
    receiving an initial diagnosis from the user; and
    moving the user to a specific location in the static diagnosing web based upon the initial diagnosis,
    wherein said initial diagnosis is received from the user while navigating through the static diagnosing web.

14. The system of claim 12, further comprising:

recording said received responses and assigning a timestamp to at least one of said received responses; and providing said received responses and one or more timestamps to facilitate record keeping and billing associated with the patient.

15. The system of claim 12 further comprising the steps of:

determining that the first working diagnosis is inconsistent with a patient reaction, moving the user via cross-connection to a new information node in the diagnosing web, wherein the new information node is not connected in the diagnosing web to a last information node navigated to prior to the first working diagnosis, collecting additional information from the user, and generating a second working diagnosis based on the collected additional information.

16. The system of claim 15, wherein the collected additional information requires repeating a test previously performed while navigating the user through the information nodes of the static diagnosing web to generate the second working diagnosis.

17. The system of claim 12 further comprising the steps of:

verifying the first working diagnosis is consistent with a patient reaction; and discharging the patient in response to the verification.

18. The system of claim 17, wherein the step of verifying the first working diagnosis comprises receiving a result of a test.

19. A non-transitory computer readable medium having a computer program stored thereon for assisting in treating a patient, wherein the computer program instructs at least one processing element to perform the following steps:

acquiring a first working diagnosis and a second working diagnosis for the patient, wherein the first working diagnosis includes a first working etiology determined by comparing a likelihood of each etiology of a plurality of possible etiologies, wherein the likelihood of each etiology is determined by a processing unit based at least in part on historical patients similar to the patient; and wherein the second working diagnosis includes a second working etiology determined by comparing a likelihood of each etiology of a plurality of possible etiologies, wherein the likelihood of each etiology is determined by a processing unit based at least in part on historical patients similar to the patient;

determining a first treatment plan, including a first set of care steps and a second treatment plan including a second set of care steps;

assigning a timestamp to each care step performed on the patient;

monitoring administration of the first set of care steps to determine whether a patient response to the first treatment plan is consistent with the first working diagnosis or the second working diagnosis; and sending, based upon a finding that the patient response is inconsistent with the first working diagnosis or the second working diagnosis, information indicative of patient response to a diagnosing engine.

20. The non-transitory computer readable medium of claim 19, further comprising:

creating a single comprehensive treatment plan configured to address the first diagnosis and the second diagnosis; and generating a set of care steps associated with said comprehensive treatment plan by the at least one processing element by consolidating redundant care steps present in both the first treatment plan for the first diagnosis and the second treatment plan for the second diagnosis.

* * * * *